(12) United States Patent
Cusí Navarro

(10) Patent No.: US 12,194,207 B2
(45) Date of Patent: Jan. 14, 2025

(54) AIR PURIFICATION DEVICE

(71) Applicant: GINSA ELECTRONIC, S.L., Barcelona (ES)

(72) Inventor: Joaquín Cusí Navarro, Barcelona (ES)

(73) Assignee: GINSA ELECTRONIC, S.L., Barcelona (ES)

( * ) Notice: Subject to any disclaimer, the term of this patent is extended or adjusted under 35 U.S.C. 154(b) by 900 days.

(21) Appl. No.: 17/277,404

(22) PCT Filed: Sep. 17, 2019

(86) PCT No.: PCT/ES2019/070609
§ 371 (c)(1),
(2) Date: Mar. 18, 2021

(87) PCT Pub. No.: WO2020/058547
PCT Pub. Date: Mar. 26, 2020

(65) Prior Publication Data
US 2022/0032231 A1    Feb. 3, 2022

(30) Foreign Application Priority Data

Sep. 19, 2018 (ES) .......................... ES201831414 U

(51) Int. Cl.
*A61L 9/014* (2006.01)
*A61L 9/20* (2006.01)
(Continued)

(52) U.S. Cl.
CPC .............. *A61L 9/205* (2013.01); *A61L 9/014* (2013.01); *B01D 46/0049* (2013.01); *B01D 46/0086* (2013.01); *B01D 46/4245* (2013.01); *B01D 46/429* (2013.01); *B01D 46/46* (2013.01); *B01D 46/62* (2022.01); *B01D 53/007* (2013.01);
(Continued)

(58) Field of Classification Search
None
See application file for complete search history.

(56) References Cited

U.S. PATENT DOCUMENTS 4,210,429 A    7/1980  Golstein
5,678,576 A   10/1997  Nazaroff et al.
(Continued)

FOREIGN PATENT DOCUMENTS

CN    203590625 U  *  5/2014
CN    204026883 U    12/2014
(Continued)

*Primary Examiner* — Jennifer A Leung
(74) *Attorney, Agent, or Firm* — The Webb Law Firm

(57) ABSTRACT

An integrated autonomous air purification device for taking in polluted air, carrying it through the inside of the purification device where it passes through a set of filtering elements (1) that trap the dust particles contained in the air; ultraviolet-light lamps (2) that transform $NO_X$ and CO gases in the air into harmless compounds; an activated carbon filter (4) that traps and eliminates the volatile organic compounds and inorganic acidic gases; second filtering elements (5) that carry out a second filtering; and an extraction hood (6) configured to direct the air coming out of the second filtering elements (5) to at least one nozzle (7) that expels the air to the outside of the purification device.

12 Claims, 2 Drawing Sheets

(51) Int. Cl.
*B01D 46/00* (2022.01)
*B01D 46/42* (2006.01)
*B01D 46/46* (2006.01)
*B01D 46/62* (2022.01)
*B01D 53/00* (2006.01)
*B01D 53/02* (2006.01)
*B01D 53/34* (2006.01)
*B01D 53/40* (2006.01)
*B01D 53/44* (2006.01)
*B01D 53/75* (2006.01)
*B01D 53/81* (2006.01)
*B01D 53/86* (2006.01)
*F24F 8/108* (2021.01)
*F24F 8/158* (2021.01)
*F24F 8/167* (2021.01)
*F24F 8/22* (2021.01)
*F24F 11/52* (2018.01)
*F24F 11/58* (2018.01)
*F24F 13/02* (2006.01)
*F24F 13/065* (2006.01)

(52) U.S. Cl.
CPC ........... *B01D 53/02* (2013.01); *B01D 53/346* (2013.01); *B01D 53/40* (2013.01); *B01D 53/44* (2013.01); *B01D 53/75* (2013.01); *B01D 53/81* (2013.01); *B01D 53/8643* (2013.01); *F24F 8/108* (2021.01); *F24F 8/158* (2021.01); *F24F 8/22* (2021.01); *F24F 11/52* (2018.01); *F24F 11/58* (2018.01); *F24F 13/0236* (2013.01); *F24F 13/065* (2013.01); *A61L 2209/111* (2013.01); *A61L 2209/12* (2013.01); *A61L 2209/14* (2013.01); *A61L 2209/22* (2013.01); *B01D 2253/102* (2013.01); *B01D 2255/802* (2013.01); *B01D 2257/404* (2013.01); *B01D 2257/502* (2013.01); *B01D 2257/708* (2013.01); *B01D 2258/06* (2013.01); *B01D 2259/804* (2013.01); *F24F 2221/42* (2013.01)

(56) References Cited

U.S. PATENT DOCUMENTS

| | | | |
|---|---|---|---|
| 5,933,702 | A | 8/1999 | Goswami |
| 8,123,836 | B2 * | 2/2012 | Kalous .................. B01D 46/12 55/467 |
| 2004/0041564 | A1 | 3/2004 | Brown |
| 2004/0166037 | A1 | 8/2004 | Youdell et al. |
| 2006/0057020 | A1 * | 3/2006 | Tufo ......................... F24F 8/22 422/24 |
| 2007/0041882 | A1 * | 2/2007 | Roseberry .......... B01D 53/8671 422/186.3 |
| 2013/0022506 | A1 | 1/2013 | Moro Franco et al. |

FOREIGN PATENT DOCUMENTS

| | | | | |
|---|---|---|---|---|
| CN | 105737262 | A * | 7/2016 | ............. F24F 11/62 |
| CN | 106051938 | A | 10/2016 | |
| CN | 106705263 | A | 5/2017 | |
| CN | 106765631 | A * | 5/2017 | |
| CN | 107763749 | A | 3/2018 | |
| CN | 108375128 | A | 8/2018 | |
| EP | 1923242 | A1 * | 5/2008 | ........... B60H 1/3414 |
| EP | 2110145 | A1 | 10/2009 | |
| ES | 2394411 | A1 | 1/2013 | |
| ES | 2595478 | A1 | 12/2016 | |
| JP | 2016101187 | A | 6/2016 | |
| WO | 0209843 | A1 | 2/2002 | |
| WO | 2009091367 | A1 | 7/2009 | |
| WO | 2009120166 | A1 | 10/2009 | |
| WO | WO-2016189177 | A1 * | 12/2016 | ............... A61L 9/16 |

\* cited by examiner

AIR PURIFICATION DEVICE

CROSS-REFERENCE TO RELATED APPLICATIONS

This application is the United States national phase of International Application No. PCT/ES2019/070609 filed Sep. 17, 2019, and claims priority to Spanish Patent Application No. U201831414 filed Sep. 19, 2018, the disclosures of which are hereby incorporated by reference in their entirety.

DESCRIPTION

Object of the Invention

The present invention consists of an autonomous air purification device that traps and eliminates the particles and pollutant gases in the air taken in, with the aim of expelling air with a reduced pollution index, using different types of filters and photocatalytic compounds.

The use of this device intends to reduce the presence of polluted air, both for open or closed spaces, in areas that usually have a high level of pollution, therefore, the field in which this invention falls is that of air cleaning and pollution reduction devices.

Background of the Invention

In recent years, due to the increasing concentration of pollutants in urban and industrial centres, people's concern for breathing clean air has increased, so that increasingly restrictive regulations have been implemented, aimed at limiting the generation of these polluting elements.

These regulations imply the necessary investment in systems that prevent pollution at ever lower levels, by the players involved in the development of those activities carried out in industrial centres and cities.

In addition to carrying out actions aimed at limiting the pollution generated, either through restrictive regulations, or by implementing processes that generate less pollution, different types of technologies have also been developed, aimed at reducing the existing pollution in the environment in an active way, capturing the air, which can be polluted with gases or suspended particles, to return it to the environment with a lower concentration of pollutants.

Among these types of technologies, air purification devices commonly called "Totems" stand out, the purpose of which is to reduce the pollution index of the environment where they are located.

At present, there is a great variety of these types of "Totems" that differ in the cleaning and purification processes carried out, as well as in the elements that make them up.

For example, the Spanish invention ES2595478, which includes the improvements of an air purification device described in the also Spanish invention ES2394411, comprises a set of elements, inserted in a hollow structure through which the air is passed with the aim of filtering the solid particles in said air, and through components, to trap the polluting gases.

In most of these air purification devices the air is passed through filters that are capable of trapping particles called PM, (Particulate Matter) followed by the size of said particles, in micrometres, so that the $PM_{10}$, are small solid or liquid particles of dust, ash, soot, metal, cement or pollen, dispersed in the atmosphere, and the aerodynamic diameter of which is less than 10 μm.

PM particles of this type are considered polluting elements since the presence thereof alters the natural composition of the atmosphere, whether it is caused by acts of nature or by human action, reason for which they are subject to be trapped by the air cleaning devices.

The filters used to trap this type of PM can be of different types, depending on the material, purpose, and operation thereof, but they are usually classified into categories based on the efficiency for trapping particles of different diameters that they are capable of blocking.

In this way, the filters classified according to the European standard EN 779 of filtration class from G1 to G4, for coarse dust, and those of filtration class M5, M6, F7, F8 and F9, for medium and fine particles, stand out. This standard imposes an average filtration efficiency for each filtration class (G1, G2, G3, G4, M5, M6, F7, F8 and F9) as well as a minimum filtration efficiency starting from filtration class F7. Said filters comply with the EN1882 classification standard, replaced by the international standard ISO 16890:2016.

In addition to these filters, classified by the European standard EN 779, which prevent the passage of particles of different sizes, air purification devices also use filters that work with activated carbon, but the objective of which is to filter the captured air, by passing said air through chemical adsorbents, which are capable of eliminating the gases in the air with efficiencies of up to 99%.

Filters of this type are configured to absorb complex gas molecules while the simpler molecules are transformed in a chemical reaction, which by means of the same activated carbon is impregnated with potassium permanganate.

These types of filters are used because, in addition to the suspended particles, the air can also be altered with a high presence of polluting gases such as volatile organic compounds (VOC) which are chemical substances that contain carbon and that easily convert into vapours or gases, which affect people's health.

Other polluting gases very present in the urban and industrial environment are those considered greenhouse gases (GHG), such as carbon dioxide ($CO_2$), nitrogen oxides ($NO_X$), which is applied to various compounds formed by the combination of oxygen and nitrogen, ozone ($O_3$) or chlorofluorocarbons (CFCs).

Polluting gases of this type directly affect people's health, and air cleaning devices use different technologies to reduce the concentration thereof, such as photocatalytic reduction.

Photocatalysis is one of the variants of advanced oxidation processes that combines ultraviolet light and oxidation by means of a catalyst in such a way that polluting gases, odours and microorganisms are eliminated, improving air quality with very efficient energy consumption. This technology is used in purification devices to decontaminate the air of harmful substances such as $NO_X$, $SO_X$ or VOCs among others.

DESCRIPTION OF THE INVENTION

In the present description, an integrated autonomous air purification device is defined that can be used in outdoor spaces, such as urban furniture, or in indoor spaces, with the aim of reducing existing pollutants in the air.

The air purification device reduces the concentration of both solid particles and gases dispersed in the environment, purifying the air to create clean environments that favour people's breathing, by means of filtering particles in three stages, large, medium and fine, whereby reducing the risks of vascular and respiratory diseases related to air pollution.

The technology used reduces pollutants by capturing and/or breaking them down into other harmless compounds. Said pollutants are suspended particles (PM) of different sizes dispersed in the air, gases such as nitrogen oxides $NO_X$, volatile organic compounds, CO, ozone, or sulphur oxides, such that the technology of the purification device acts as a trapping mesh from devices, to generate clean air paths, reducing pollution both outdoors and inside buildings.

The autonomous integrated air purification device is configured in such a way that it comprises intake means, the purpose of which is to take in a high volume of air located in the vicinity of the device, whether said device is located indoors or in an outdoor environment, wherein said air can have a large presence of polluting particles and gases, and carry it through the inside of the air purification device, wherein the concentration of these pollutants is reduced by being trapped and eliminated by the elements comprised by the purification device.

These elements comprised by the air purification device are:
- first filtering elements configured to trap the coarse dust particles contained in the outside air such as soot, as well as small leaves or small pieces of paper, but enabling the passage of the air taken in through the intake means, to the purification device;
- ultraviolet-light lamps located in ducts impregnated with a photocatalytic compound, configured to, in combination with the ultraviolet light, transform the $NO_X$ and CO gases, by means of a photocatalytic reduction of acidic gases contained in the air coming out of the first filtering elements, into harmless compounds.
- The ducts, preferably with a rectangular cross section, comprise the ultraviolet-spectrum light lamps inside thereof, and are considered obstructions because they hinder the normal passage of the air through the inside of the device, transforming the laminar air flow into a turbulent one, thereby increasing the speed and in turn promoting greater contact between the air and the walls of the ducts, which are impregnated with a photocatalytic substance;
- an activated carbon filter configured to trap and eliminate the volatile organic compounds and inorganic acidic gases contained in the air that has passed through the ducts. This trapping is carried out by means of the adsorption, absorption or oxidation of particles of said gases depending on the type of pollutant but enabling the passage of air at the same time;
- second filtering elements configured to enable the passage of the air coming out of the activated carbon filter, but to trap the passage of particles, solid or liquid, contained in said air coming out of the activated carbon filter, and;
- an extraction hood configured to direct the air coming out of the second filtering elements to at least one nozzle that expels said air to the outside of the purification device, by means of the propulsion generated by at least one motor. This expulsion of air is carried out at high speed to launch it over a long distance, preventing it from being taken in again, and with the aim of connecting the air flow created with other nearby purification devices, generating a stream of clean air.

The operation of the purification device consists of taking in the outside air, which may have a high concentration of solid particles and polluting gases, causing it to enter through the lower portion of the device, having to pass through the trapping elements, so that it goes up, thanks to the depression created by the intake means and the expulsion motor, until it is expelled through the upper end of the device through the nozzle, with a lower concentration of pollutants.

Specifically, once the air has been filtered by the first filtering elements, it is circulated through a plate that carries it through the rectangular ducts that house the ultraviolet-light lamps to then pass through the activated carbon filter, where the total filtering is carried out, and the second filtering elements, which trap the particles that may have come off other filters.

Once the air has passed through all the filtering elements it is expelled, so that the performance of the device depends on the concentration ratio of the outlet and inlet pollutants, the performance being higher the higher the inlet pollutant concentration.

In an embodiment, the purification device has a rectangular prism structure in a vertical position that comprises means for lifting off the ground or legs on which it is supported, the lower surface or base possibly being uncovered. Said lower surface or base, enables the air to enter the purification device through a first coarse particle trapping barrier, generated by the intake means, in a flow regime between 100 and 30.000 $m^3/h$ of air, depending on the selected device.

In an embodiment, the first filtering elements, which act as the first particle traps, comprise at least two trapping means:
- a first trapping means for coarse dust, which carries out the pre-filtering of the integrated air purification device, trapping particles greater than 10 μm in diameter and that is comprised of at least a first G2 type filter and a second G4 type filter with high capacity broken surface and;
- a second trapping means for fine dust, comprised of a third M6 type filter, comprising glass microfibres, configured to accumulate the trapped dust.

The first G2 type filter is configured to trap particles with an average arrestance (aA) against synthetic dust comprised between 65% and 80%, the second G4 type filter with an average arrestance greater than 90%, and the third M6 type filter with an average efficiency (aE) against particles of 0.4 μm of between 60%≤aE<80%, the arrestance being the efficiency of a filter, based on the total weight of the captured particles, regardless of the particle size. In other words, arrestance represents a measure of a filter's ability to capture large particles (10 microns and larger).

In an embodiment, the rectangular obstructions are configured to increase the speed of the air flow that comes out of the first filtering elements and to convert said flow into a turbulent one, such that it is increased the contact of said air with the rectangular ducts wherein the photocatalytic material is located. This increase in air speed is due to the fact that the presence of the ducts limits the cross section of the air passage, and at a constant inlet flow, the speed increases.

In an embodiment, the activated carbon filter that traps and eliminates the volatile organic compounds and inorganic acidic gases in the air that has flowed through the rectangular obstructions, comprises granules that are impregnated with alumina, to improve the ability thereof to neutralise toxic gases.

In an embodiment, the second filtering elements are comprised of at least one G4 type filter, with an average arrestance (aA) greater than 90%, configured to trap any particle that has come off from the first filtering elements and from the activated carbon filter and an F9 type filter, with an average efficiency (aE) against 0.4 μm particles greater than 90%, which is configured to trap 99% of the $PM_{10}$, $PM_5$ and $PM_{2.5}$ particles. In other words, these second filtering elements limit the size of the air particles even more than the first filters.

In an embodiment, the nozzle that expels the air from the purification device is configured to manually or automatically vary the air outlet direction, by being connected to said purification device by means of ball joints. These joints enable the nozzle to rotate in any direction of space, without being limited to axes.

In an embodiment, the air purification device comprises a first set of sensors configured to measure in real time, at least one of the environmental parameters of temperature, pressure, humidity, gas concentrations of $NO_X$, $SO_X$, $CO_X$, $O_3$, acetylene, liquefied gas, VOC's, as well as concentrations of $PM_{10}$ in parts per billion (ppb) and in mg/m³ of the outside air taken in by the intake means of the integrated autonomous device as well as of the air expelled by the nozzles, once purified.

In an embodiment, the air purification device comprises a second set of sensors configured to measure the clogging of the first and second filtering elements by means of the initial and operating pressure difference of the air flow that passes through said compartments.

In an embodiment, the purification device comprises at least one computer system and one interactive monitor configured to display information on at least some of the parameters that define the operation of the device and the parameters provided by the reading of the sensors comprised by the device.

In an embodiment, the monitor is also configured to operate as a control device for the device and is able to put it into operation, selecting the available options of the device, by way of a touch screen, the device being connected to the computer system.

This monitor can also be used to display additional information, alternative to the operation of the device, depending on the user's preferences. In other words, the device has the ability to operate as a communicating means by the interactive screen that enables information of interest to be displayed to the users, such as air quality, public announcements, citizen information or advertising.

In an embodiment, the purification device comprises at least one universal connector (USB) configured to connect the autonomous purification device to an electronic device by means of cable, to charge the battery of electronic devices, and to upload and download data from the device to a storage device.

In one embodiment, the purification device comprises connection means that can be 3G connectivity, 4G connectivity, LAN connection or WIFI connectivity, which are configured to transmit and process the values of the readings of the sensors, and to remotely control and manage the device.

The device is configured to be able to integrate into multiple environments as the structure has the possibility of being built in different materials, such as metals, glass or ceramic materials, depending on the environment and the possible alterations that the user may cause to the device. In addition, it can incorporate more than one monitor or digital screen adapted to the environment, lighting elements or decorative elements that facilitate the adaptation thereof to the environment.

DESCRIPTION OF A PREFERRED EMBODIMENT

Figure 1:
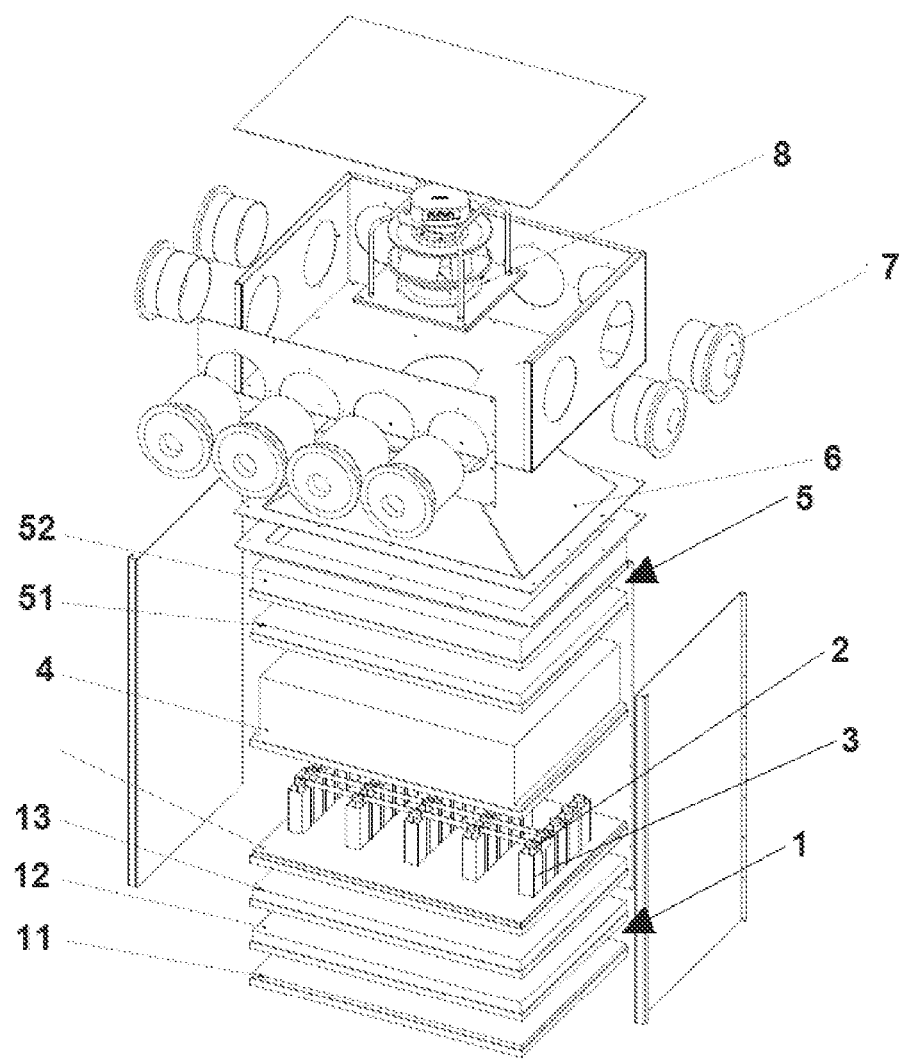
FIG. 1 shows an exploded perspective of the air purification device, enabling observing all the components comprised by said purification device.

As can be seen in FIG. 1, the invention consists of an autonomous air purification device wherein the air is captured through the lower portion and passes through different filtering elements that capture and/or destroy the pollutants. Finally, the cleaned or purified air is released through the nozzles (7) located in the upper portion, to the outside.

The assembled device has a rectangular prismatic shape and is located in a vertical position, so that the inlet of the outside air, which can be polluted with both solid and liquid and gaseous particles, is carried out through the lower portion of said device, through a first coarse particle trapping barrier that facilitates the air intake but prevents the inlet of large lightweight elements such as sheets or plastics into the device.

To trap the inlet of solid particles dissolved in the air into the device, there are first filtering elements (1) located above the first coarse particle trapping barrier, which has two trapping means:
  a first coarse particle trapping means that has two filters in the direction of air flow:
    a first G2 type filter (11) to prevent the passage of coarse elements
    a second G4 type filter (12) with high capacity broken surface, for smaller elements such as soot.
  Above these filters, there is a second trapping means consisting of a third M6 type filter (13) with special glass microfibres that guarantee a low initial charge drop and an excellent capacity for accumulating particles.

By having three filters (11, 12 and 13) consecutively arranged, with different degrees of efficiency and arrestance, trapping is achieved in stages depending on the size of the particles, so that the filters (11, 12 and 13) are prevented from clogging quickly and requiring maintenance at short intervals.

The air coming out of the first filtering elements (1) flows through a plate that carries it through rectangular ducts (3) comprising ultraviolet-light lamps (2) inside them. The walls of these ducts (3) are impregnated with a layer of a photocatalytic compound that in combination with ultraviolet light causes the destruction of $NO_X$ and CO.

Figure 2:
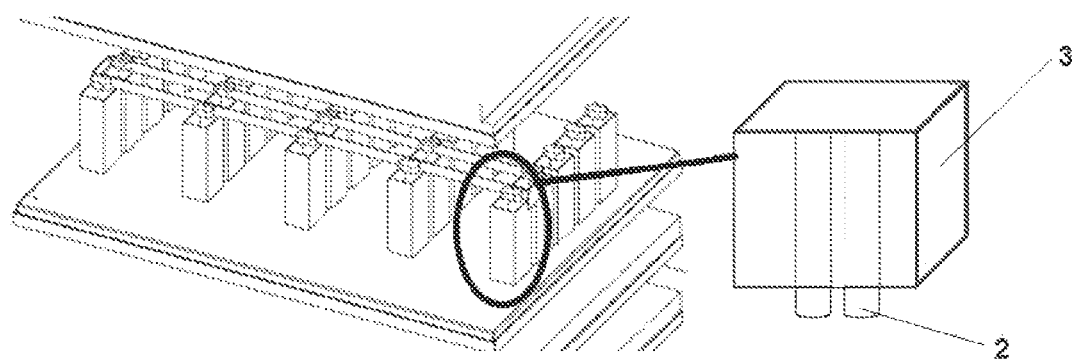
FIG. 2 shows a detail of the rectangular obstructions with the ultraviolet-light lamps inside.
Figure 3:
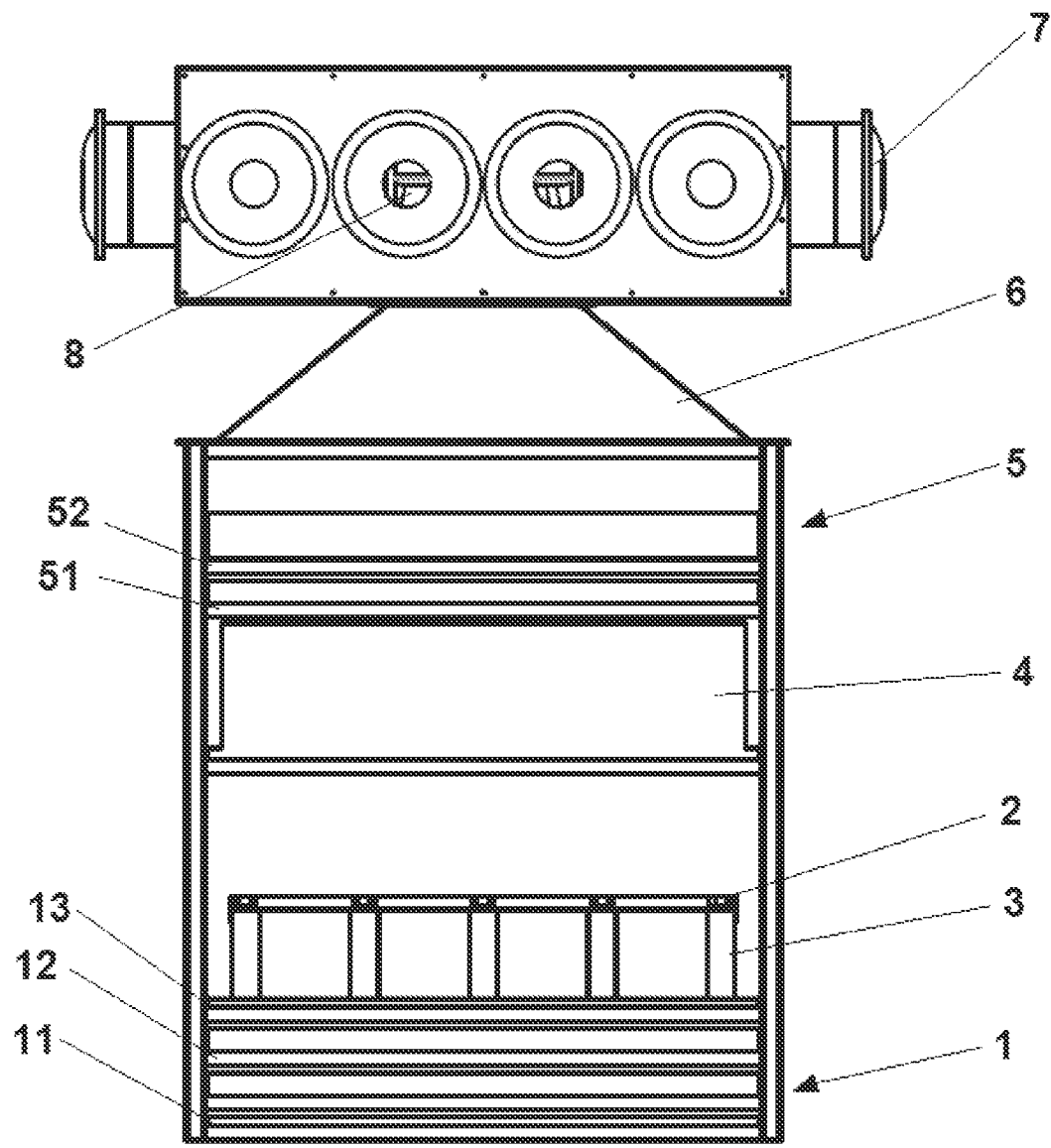
FIG. 3 shows an elevated perspective of the complete assembled device.

The air flow enters these ducts (3) or cavities at a higher speed due to the design of the ducts (3) and the constriction of passage with a constant flow, causing the flow to become a turbulent one, which maximises the contact between the air mass and the walls wherein the photocatalytic material is located, as shown in FIG. 2.

As can be seen in exploded FIG. 1, there is an activated carbon filter (4) in the upper portion of the rectangular ducts (3), half of said activated carbon being impregnated with alumina and the other half in a virgin state.

By means of this filter (4) the adsorption, absorption and/or oxidation for trapping and/or destroying VOCs and inorganic acidic gases such as $NO_X$ or $CO_2$ of the air that has flowed through the rectangular ducts is achieved. Likewise, the elements that have not finished reacting in the photocatalysis step are removed and trapped in this filter.

The second filtering elements (5) are located in a position above the activated carbon filter (4). A fourth G4 type filter

(51) and a fifth F9 type filter (52) that trap the possible elements that may have come off from the previous filters and ensure an elimination close to 99% of the $PM_{10}$, $PM_5$ and $PM_{2.5}$ particles.

Once the air has passed through the second filtering elements (5) and is clean, it is carried by means of a hood (6) to a motor (8) that projects it at high speed through a series of nozzles (7) that are located on the sides of the upper portion of the device, so that the air is expelled at a distance of between 10 and 50 metres, to prevent the clean air from being taken in again, and to try to interlace the air flows with other devices, according to the arranged configuration.

The working ranges of the purification device are 24 hours a day, although they may depend on the weather conditions and atmospheric pollution, since, in case of taking in clean air, it is not necessary to carry out the purification processes.

To check the correct operation of the air purification device, a series of sensors are arranged to measure in real time environmental parameters such as temperature, pressure, humidity, concentrations of inlet pollutant gases or of dispersed solid particles, of the outside air taken in and of the air expelled through the extraction hood, as well as sensors to measure filter wear, relating the concentration of the amount of trapped particles with respect to the surface of the filtering elements in $mg/m^2$.

To make the information read by these sensors known to the user, the device comprises a computer system connected to said sensors and to 4 interactive monitors located on the sides of the device, further configured to operate as a means of communication through the interactive screen, displaying information of interest to the users, such as air quality, public announcements, citizen information or advertising.

To facilitate the operation of the computer system, the device comprises USB type universal connectors, to connect to other electronic devices, to charge the battery or to exchange data from the device to the electronic device.

The device also comprises means of wireless connection such as 3G, 4G, or WIFI connectivity, or by means of cable via LAN connection, for the input and output of data from the device, and to be able to be controlled remotely.

The invention claimed is:

1. An autonomous integrated air purification device comprising intake means, configured for taking in an outside air with particles, as dust particles, and polluting gases, as $NO_X$, CO, volatile organic compounds, and inorganic acidic gases, and carrying the outside air through the inside of the air purification device, wherein the outside air taken in by the intake means is an inlet air of the air purification device, the purification device further comprising:
   first filtering elements configured to trap dust particles contained in the inlet air of the purification device and to enable passage of the inlet air;
   ultraviolet-light lamps inside rectangular ducts, wherein the ducts are impregnated with a photocatalytic compound configured for, in combination with ultraviolet light generated by the ultraviolet-light lamps, transforming the $NO_X$ and CO gases contained in an air coming out of the first filtering elements into harmless compounds, and wherein the rectangular ducts are oriented in a parallel direction and situated in a rectangular matrix shape distributed in rows and columns;
   an activated carbon filter configured to trap and eliminate volatile organic compounds and inorganic acidic gases contained in the air that has passed through the rectangular ducts;
   second filtering elements configured to enable the passage of the air coming out of the activated carbon filter and to trap the passage of particles contained in the air coming out of the activated carbon filter; and
   an extraction hood configured to direct the air coming out of the second filtering elements to at least one nozzle configured to expel the air to the outside of the purification device at a distance of between 10 and 50 meters, by means of propulsion generated by at least one motor, to prevent the expelled air from being taken in again by the intake means,
   wherein the inlet air enters through a lower end of the purification device and goes up, passing through the elements that make up the device, to come out of the device through an upper end through to at least one nozzle with a lower concentration of particles and polluting gases than a concentration of the inlet air.

2. The air purification device according to claim 1, further comprising a rectangular prism structure in a vertical position which comprises means for lifting off the ground and a perforated lower surface through which the outside air is taken by the intake means.

3. The air purification device according to claim 1, wherein the first filtering elements comprise at least two means for trapping particles, the at least two means for trapping particles comprising:
   a first retention means, configured to filter the inlet air, trapping particles greater than 10 μm in diameter, the first retention means comprising at least:
      a first filter selected from a G2 filter; and
      a second filter selected from a G4 filter, the G4 filter having a broken surface; and
      a second trapping means, comprised of a third filter selected from a M6 filter, the M6 filter comprising glass microfibres configured to accumulate the trapped dust particles.

4. The air purification device according to claim 1, wherein the rectangular ducts are configured to increase the speed of the air flow coming out of the first filtering elements and to convert the air flow into a turbulent one, increasing the contact of the air with the rectangular ducts, where the photocatalytic compound is located.

5. The air purification device according to claim 1, wherein the activated carbon filter comprises granules that are impregnated with alumina.

6. The air purification device according to claim 1, wherein the second filtering elements further comprises:
   a fourth filter selected from a G4 filter, configured to trap any particle that has come off from the first filtering elements and from the activated carbon filter; and
   a fifth filter selected from a F9 filter configured to trap 99% of $PM_{10}$, $PM_5$ and $PM_{2.5}$ particles.

7. The air purification device according to claim 2, wherein the at least one nozzle is configured to expel the air to the outside of the device and configured to vary an air outlet direction, as the at least one nozzle is connected to the rectangular prism structure of the purification device by means of a ball-and-socket joint.

8. The air purification device according to claim 1, further comprising a set of sensors configured to measure in real time, at least one environmental parameter selected from: temperature, pressure, humidity, and gas concentrations of $NO_X$, $SO_X$, $CO_X$, $O_3$, and $PM_{10}$, in ppb and in $mg/m^3$, of the air taken in by the intake means of the integrated autonomous air purification device.

9. The air purification device according to claim 1, further comprising a set of sensors configured to measure the wear of at least one of the filters.

10. The air purification device according to claim 1, further comprising a computer system and at least one interactive monitor configured to display information.

11. The air purification device according to claim 1, further comprising at least one Universal Serial Bus (USB) configured to:
- connect the purification device by means of cable to an electronic device;
- charge a battery of an electronic device; and
- carry out a data transfer from the purification device to a storage device.

12. The air purification device according to claim 1, further consisting connection means selected from the group comprising of 3G connectivity, 4G connectivity, LAN connection, and WIFI connectivity.

* * * * *

UNITED STATES PATENT AND TRADEMARK OFFICE
CERTIFICATE OF CORRECTION

PATENT NO. : 12,194,207 B2
APPLICATION NO. : 17/277404
DATED : January 14, 2025
INVENTOR(S) : Joaquín Cusí Navarro Page 1 of 1

It is certified that error appears in the above-identified patent and that said Letters Patent is hereby corrected as shown below:

In the Claims

Column 9, Line 16, Claim 12, delete "consisting" and insert -- comprising --

Column 9, Line 17, Claim 12, delete "comprising" and insert -- consisting --

Signed and Sealed this
Twenty-fifth Day of March, 2025

Coke Morgan Stewart
*Acting Director of the United States Patent and Trademark Office*